US005583782A

United States Patent [19]

Heaven et al.

[11] Patent Number: 5,583,782
[45] Date of Patent: Dec. 10, 1996

[54] CALIPER PROFILE CONTROL SYSTEM FOR PAPER MACHINE PROVIDING REDUCED START UP TIMES

[75] Inventors: Edwin M. G. Heaven, North Vancouver; Christopher B. Lynch, Burnaby; Par O. A. Hallman, North Vancouver, all of Canada

[73] Assignee: Measurex Devron Inc., North Vancouver, Canada

[21] Appl. No.: 337,249

[22] Filed: Nov. 10, 1994

[51] Int. Cl.$^6$ .................................................. G06F 19/00
[52] U.S. Cl. ................ 364/471.03; 100/50; 364/469.01
[58] Field of Search ............................... 364/469, 470, 364/471, 563, 571.02; 100/47, 48, 50; 162/252, 253, 254, 258, 262, 263

[56] References Cited

U.S. PATENT DOCUMENTS

| | | | |
|---|---|---|---|
| 4,114,528 | 9/1978 | Walker | 100/47 |
| 4,680,089 | 7/1987 | Aral et al. | 162/198 |
| 4,707,779 | 11/1987 | Hu | 364/148 |
| 4,903,528 | 2/1990 | Balakrishnan et al. | 73/159 |
| 4,947,684 | 8/1990 | Balakrishnan | 73/159 |
| 4,965,736 | 10/1990 | Balakrishnan | 364/469 |
| 4,982,334 | 1/1991 | Balakrishnan | 364/469 |
| 5,121,332 | 6/1992 | Balakrishnan et al. | 364/471 |
| 5,170,357 | 12/1992 | Sasaki et al. | 364/471 |
| 5,298,122 | 3/1994 | Munch et al. | 364/471 |

Primary Examiner—Roy N. Envall, Jr.
Assistant Examiner—Brian C. Oakes
Attorney, Agent, or Firm—Christie, Parker & Hale, LLP

[57] ABSTRACT

A caliper profile control system for a paper machine provides reduced start up times after sheet breaks to bring the caliper profile across the sheet to within the desired limits. The method comprises the steps of scanning at predetermined intervals across the width of the paper sheet to monitor thickness error of the sheet from predetermined limits and change in the thickness error between the intervals, in each of a plurality of zones across the sheet. A control change signal is determined for each of the zones based on the error and the change in error using an exponential function of the magnitude of the error to maximize the change in the error and reduce integral action when the error is large. The control signal is used to reduce the error in each zone and the integral action is increased as the error decreases until the predetermined limits are met.

5 Claims, 2 Drawing Sheets

CALIPER PROFILE CONTROL SYSTEM FOR PAPER MACHINE PROVIDING REDUCED START UP TIMES

TECHNICAL FIELD

The present invention relates to controlling caliper profile of a paper sheet produced on a paper machine and more specifically to a control system which reduces the recovery time or start up time to bring the caliper profile across the width of a paper sheet to within predetermined limits after a sheet break.

BACKGROUND ART

The thickness of paper sheet is referred to as caliper and the caliper profile refers to the thickness profile across the width of the sheet. Caliper profiles are measured by scanning devices located downstream of a series of rolls arranged in parallel, one above the other in a stack. The sheet material passes through the space between adjacent rolls known as a nip. Such rolls are generally defined as calender rolls and the caliper profile is changed by adjusting the spacing between adjacent rolls, and by controlling the nip pressure and the surface roll temperature. These two control systems are interdependent and both systems are able to control in a series of zones along the length of the rolls to ensure that the paper sheets have a substantially uniform caliper profile across the paper width.

One example of a calender control system for sheet making is shown in U.S. Pat. No. 4,982,334, assigned to Measurex Corporation. As can be seen, the scanning device produces a signal representing caliper profile across the width of a paper sheet. This signal is then split into a high frequency signal and low frequency signal. The low frequency signal, which represents coarse control, is fed to what is referred to as a crown roll. This is a hollow roll containing internal hydraulic mechanisms to exert hydraulic pressure to change the curvature laterally along the length of the roll and thus the nip pressure is varied along the roll. In practice the hydraulic mechanisms can either cause the lateral surface of the crown roll to have a convex, flat or concave shape. In some cases sectionalized crown rolls are used, dividing the roll into a series of zones. However, in most cases the control system is reasonably coarse simply because it changes the shape of the roll overall.

The high frequency control is fed to a series of individual heaters positioned on zones extending along the length of a roll. The heaters apply heat to vary the surface temperature of the roll in each zone, and the roll expands or contracts in that zone to vary the paper sheet thickness in that zone. These heating devices may be used on a crown roll or on a plain steel roll, depending on the particular arrangement of rolls in a calender stack. There are generally two types of heaters used for heating the surface of the roll. One type is an induction heater, an example of such a type is sold by Measurex Corporation under the trade mark CALCOIL. A second type of heater is what is referred to as a heated air shower, and these heated air showers blow hot air in each of the zones along the length of the roll. The temperature of the air for each shower is controlled to vary the surface temperature of the roll and consequently vary the paper sheet thickness. One example of such a type of heated air shower is sold by Measurex Corporation under the trade mark CALTROL.

The heaters provide the fine adjustment, what is referred to as high frequency adjustment, and the internal hydraulic mechanisms in a crown roll provide the coarse adjustment, what is referred to as the low frequency adjustment. When the zone of a roll is heated, the diameter increases and thus the load on a paper sheet in a nip increases. This causes a localized decrease in thickness which maintains the thickness profile at a desired target.

After a paper sheet breaks, the temperature of the roll faces change significantly due to the fact that no paper sheet is passing therethrough. Thus, when the paper is rethreaded the thickness profile is often far off the predetermined thickness limits required for the paper, so the paper is not commercially saleable. There is therefore a requirement to return caliper profile for a paper sheet to within the predetermined limits in as short a time as possible, thus avoiding paper wastage.

Control systems presently used to control the caliper profile following signals received from a scanning device do not compensate for the process behaviour during heating. This results in control signal windup which can cause the process to overshoot the target. The initial error from target at start up is usually quite large and generally made up of large humps and valleys in the caliper profile. The low frequency thickness variation is ideally suited to the hydraulic load cylinders inside a crown roll which react quickly. However, the high frequency control which involves varying the heat of the roll surface has a slower reaction time. Once the low frequency target has been met, then the high frequency errors from the target are still too large and must be attacked with the finer control utilizing heaters. The high frequency control system is generally limited by the speed at which the roll surface can be heated. When heat is applied to one zone, the temperature and therefore the roll diameter, increases following a ramp trajectory. The shape of this ramp changes with the amount of heat applied, and the resulting effect is to have an overshoot, thus the thickness of the paper sheet in that zone becomes too thin. To avoid an overshoot, it is necessary to provide a system wherein the maximum reduction in the error of the caliper profile in one zone occurs, but the caliper in that zone does not go either under or over the target, namely the predetermined limits.

It is an aim of the present invention to provide a method of reducing start up times after a break in a paper sheet on a paper machine to bring the caliper profile across the width of the paper sheet to within predetermined limits as fast as possible. It is also an aim of the present invention to provide a control system which reduces start up time to bring the caliper profile to within acceptable quality limits after a machine break, and to co-ordinate the use of various actuators to control heaters and heating and cooling rates of rolls to reduce the recovery time or start up time.

It is also an aim of the present invention to use an adaptive control scheme to bring the caliper profile of a paper sheet to within the predetermined limits as fast as possible without overshooting the predetermined limits and thereafter to maintain control of the caliper within the predetermined limits.

DISCLOSURE OF INVENTION

The present invention provides a method of reducing start up time for bringing caliper profile across a width of a paper sheet to within predetermined limits on a paper machine, comprising the steps of: scanning at predetermined intervals across the width of the paper sheet to monitor thickness error of the sheet from the predetermined limits, and change in the thickness error between the intervals, in each of a plurality of zones across the sheet, determining a control change signal in each of the zones based on the error and the change in the error using an exponential function of the magnitude of the error to maximize the change in the error and reduce integral action when the error is large, utilizing the control change signal to reduce the error in each of the zones, and increasing the integral action in each of the zones as the error decreases until the predetermined limits are met.

There is also provided in the present invention a method of reducing start up time for bringing a caliper profile across a width of a paper sheet to within predetermined limits on a paper machine, comprising the steps of: scanning at predetermined intervals across the width of the paper sheet to provide an error signal representing caliper profile across the sheet, splitting the error signal into a high frequency signal and a low frequency signal, utilizing the low frequency signal to control the caliper profile within predetermined low frequency limits, continuing scanning at predetermined intervals across the width of the paper sheet to provide high frequency signals representing thickness error of the sheet from predetermined high frequency limits, and change in the thickness error between the intervals, in each of a plurality of zones across the sheet, determining a control change signal in each of the zones based on the error and the change in the error using an exponential function of magnitude of the error to maximize the change in the error and reduce integral action when the error is large, utilizing the control change signal to reduce the error in each of the zones, and increasing the integral action in each of the zones as the error decreases until the predetermined high frequency limits are met.

In another embodiment a control system is provided which reduces start up time to bring caliper profile across a width of a paper sheet to within predetermined limits on a paper machine comprising: scanning means to scan across the width of the paper sheet at predetermined intervals and produce error signals representing thickness error of the sheet from the predetermined limits in a plurality of zones across the sheet, means to determine change in the error in each of the zones from scan to scan, optimizer means to maximize the change in the error in each of the zones, when the error is large, by modifying the change in error as a function of the error to provide a control change signal which is limited, based on magnitude of the error, by reducing integral action when the error is large, the integral action increasing as the error decreases, and control means utilizing the control change signal to reduce the error in each of the zones until the predetermined limits are met.

BRIEF DESCRIPTION OF DRAWINGS

In drawings which illustrate embodiments of the present invention.

BEST MODE FOR CARRYING OUT THE INVENTION

Figure 1:
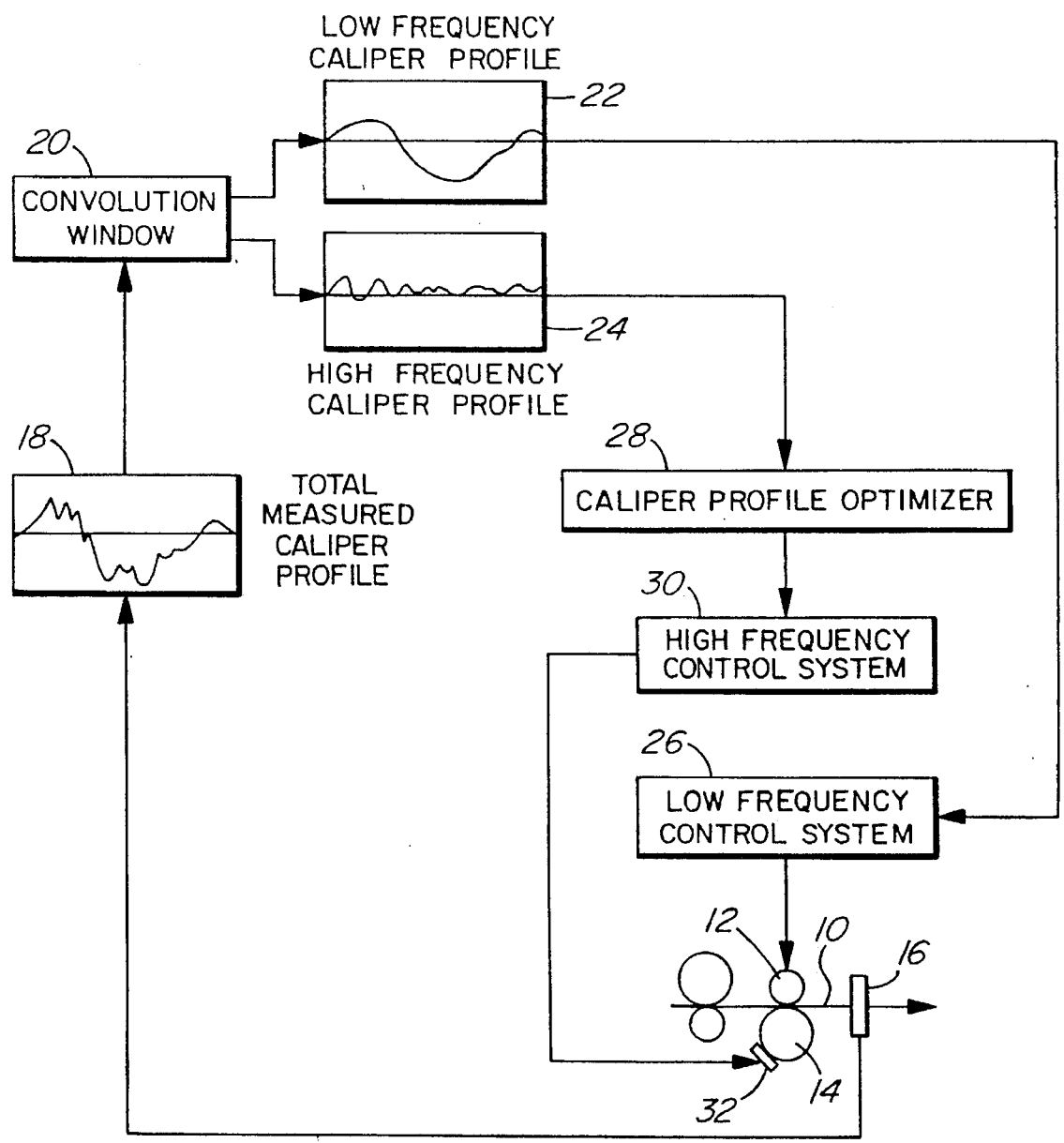
FIG. 1 is a schematic drawing illustrating a scanning device and splitter to provide a low frequency and high frequency caliper profile and showing a high frequency control system and a low frequency control system, the high frequency control system having a caliper profile optimizer according to an embodiment of the present invention.

A control system for the caliper profile of a paper sheet is illustrated in FIG. 1 wherein a paper sheet 10 is shown passing through a nip in a top crown roll 12 and a bottom roll 14. A scanning device 16 is shown downstream of the rolls 12,14 and a profile 18 is shown produced by the scanning device representing a combination of low frequency and high frequency caliper profile. The signal from the scanning device 16 is split by a convolution window 20 to produce a low frequency caliper profile 22 and a high frequency caliper profile 24. The low frequency caliper profile provides a signal to the low frequency control system 26 which in turn controls the hydraulic mechanisms (not shown) within the top crown roll 12. The high frequency caliper profile signal passes first to a caliper profile optimizer 28 which in turn provides a control change signal to a high frequency control system 30, and this in turn controls the heaters 32 which apply heat to zones extending along the length of the roll 14 and thus controlling the caliper profile across the width of a paper sheet 10 passing between the nip of rolls 12,14.

Figure 2:
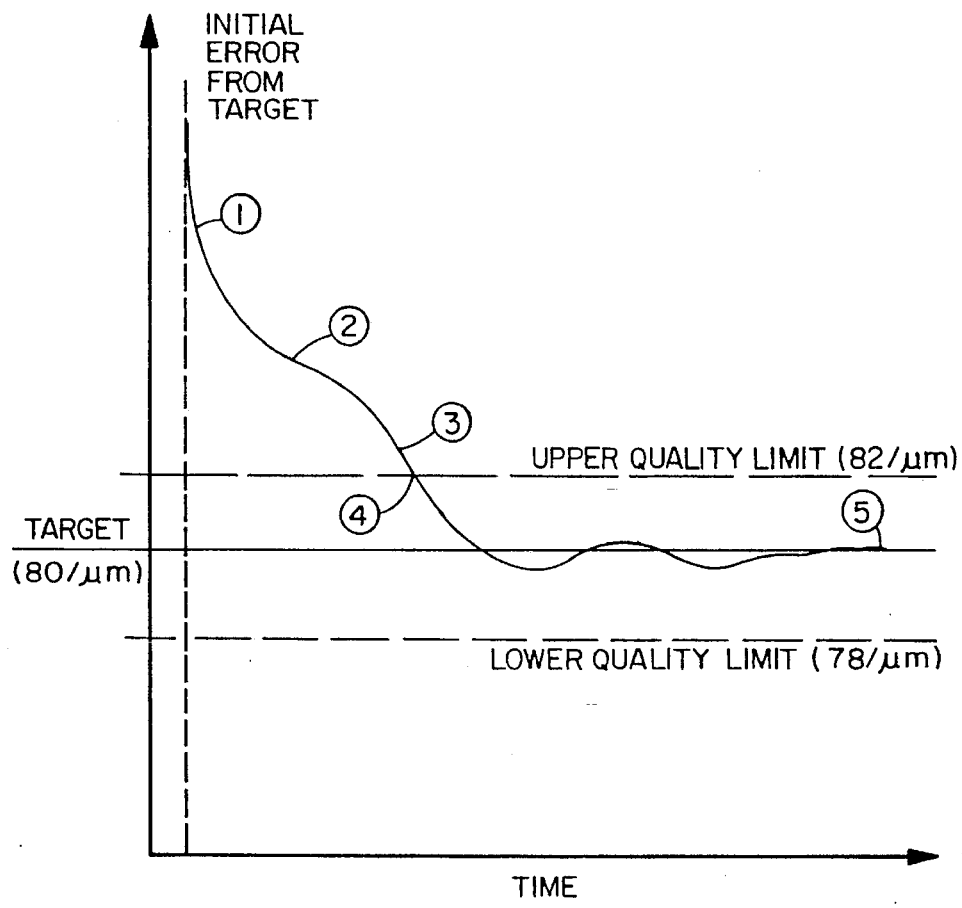
FIG. 2 is a graph showing thickness error of a paper sheet from start up versus time.

After start up, or following a paper sheet break, the low frequency thickness control reacts reasonably quickly to bring the caliper profile to within the required low frequency range. However, removal of the remaining error, which represents the high frequency thickness error, is dictated by the rate at which the roll 14 can be heated. This is accomplished by first accelerating the heating rate to thin the paper sheet and bring it towards the predetermined limits of caliper profile in each of the zones, and then limiting (braking) the heating before the target is reached. By controlling the amount of (acceleration) heating and the amount of (braking) reduction in heating, the target is reached without significantly being passed. Such an example is shown in FIG. 2 wherein the target is shown as being 80 μm with an upper quality limit of 82 μm and a lower quality limit of 78 μm. The error from target is shown on the Y axis plotted against time and, as can be seen, initially the control occurs from the low frequency system by utilizing an internal hydraulic mechanism within a crown roll 12 (1). Following this the high frequency control system cuts in, the heating in a particular zone is shown gradually increasing (2) until it reaches maximum power (3) and then braking action occurs (4) as it reaches the upper quality limit. The caliper then gradually decreases, the overshoot dies out (5) and the target line is reached for each of the zones.

The control system continuously monitors the error and changes in error in each of the zones and adapts amount of acceleration or braking based on an exponential function of the absolute value of the error.

The thickness error is measured in each of the zones across the paper sheet and the change in the error from one scan to the next in each of the zones is determined. A control change signal is then calculated based on the error and the change in the error. The larger the change in the error, the larger the control change signal. However, the size of the control change signal does not increase as the error increases, its contribution is scaled using an exponential function of the magnitude of the error. The control change signal is sent to individual actuators for the heaters in each of the zones. The magnitude of the control change signal in each of the zones is based on the magnitude of the error by reducing integral action when the error is large and increasing the integral action in each of the zones as the error decreases until the predetermined limits are met.

In each zone, the control change signal is determined according to the formula:

$$c(t)=K_p[(e(t)-e(t-1))+K_I e(t)]$$

where $K_p$ is a process gain factor dependent upon the particular heating system utilized in the different zones on the roll and upon the type of roll being heated, e(t) represents the error for one scan and e(t−1) represents the error for the previous scan. $K_I$ is a function of the error and equals:

$$\exp\frac{(-e(t))}{\lambda} \times K_{IO}$$

where $K_{IO}$ is the nominal $K_I$ gain when the error is small, and $\lambda$ is a gain scaling factor that modifies the fraction of $K_{IO}$ used at different error magnitudes.

Utilizing the control equation avoids overshoot by reducing the integral action when the error is large. The scaling of the integral action is controlled by the choice of $\lambda$. As the error in each zone decreases, the amount of integral action is increased until the nominal value is obtained. This prevents windup of the control signal and caliper overshoot while ensuring that no constant error exists in the caliper profile. The choice of $\lambda$ is related to the quality objectives; typically the quality limits, and the choice gain is related to the response rate desired, the type of heaters being used, and the type of roll being heated.

Figure 3:
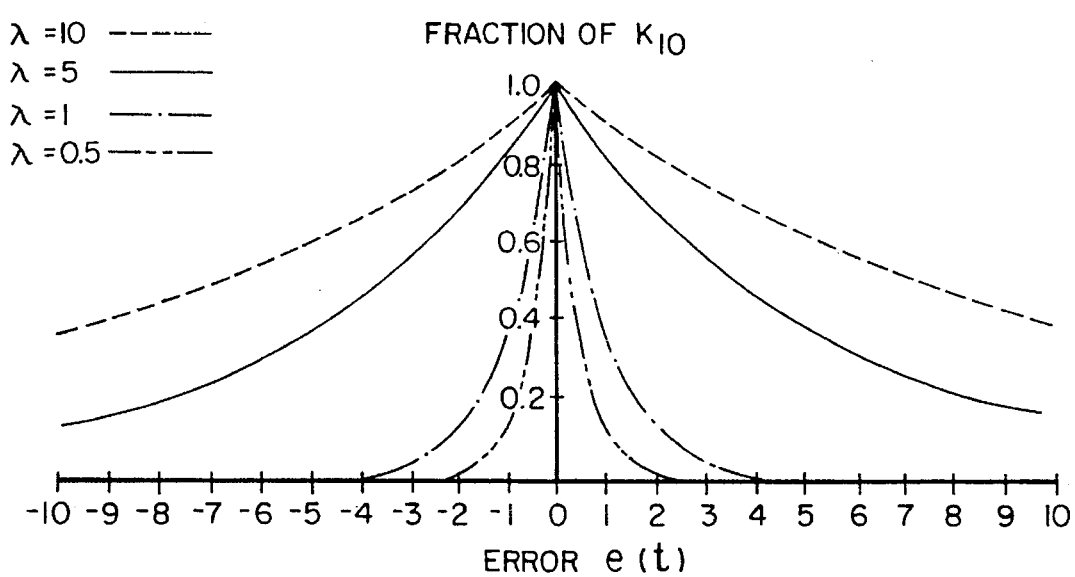
FIG. 3 is a graph showing the influence of various gain scaling factors for the amount of integral action used, which is a function of the error, for different magnitudes of error.

As shown in FIG. 3, the influence of the gain scaling factor ($\lambda$) on the amount of integral action, which is a function of the error, is plotted against different magnitudes of the error. The gain scaling factor is shown varying from 0.5 to 10, thus when the error equals the gain scaling factor, 38% of $K_{IO}$ is always used. Thus, all of $K_{IO}$ is used when the error is zero but once the error is larger than four times $\lambda$, then there is no integral action used at all.

It is known that the caliper change caused by the induction heaters in the individual zones is inherently non-linear, both in terms of gain and time constant. The direction of the change, i.e., more or less heating, affects both the magnitude and speed of the change. Thus, by utilizing the equation a Table of control change signals is produced for error magnitudes and change in error magnitudes to suit particular types of heaters.

TABLE 1

Table of Control Changes $\Delta e(t)$

```
     10, 8, 5, 5, 5, 5, 5, 5, 5, 5, 5, 5, 5, 5, 5, 5, 4, 4, 4
      8, 5, 5, 5, 5, 5, 5, 5, 5, 5, 5, 5, 5, 4, 4, 4, 3, 3, 4
      5, 5, 5, 5, 5, 5, 5, 5, 5, 5, 5, 5, 4, 4, 3, 3, 3, 3, 4
      5, 5, 5, 5, 5, 5, 5, 5, 5, 4, 4, 4, 3, 3, 2, 2, 3, 3, 3
      5, 5, 5, 5, 5, 5, 4, 4, 4, 3, 3, 3, 2, 2, 1, 1, 2, 2, 3
      4, 4, 4, 4, 4, 4, 4, 3, 3, 2, 2, 2, 1, 1, 5, 1, 1, 2, 2
      4, 4, 4, 4, 3, 3, 3, 3, 2, 1, 1, 1, 5, 5, 5, 5, 1, 1, 1
      4, 4, 3, 3, 3, 2, 2, 2, 1, 5, 2, 5, 0, 0, 0,-2,-5,-1,-1
      3, 3, 3, 2, 2, 2, 1, 1, 5, 2, 0, 0, 0,-2,-5,-5,-1,-2,-2
e(t)  3, 2, 2, 1, 1, 5, 2, 2, 0, 0, 0,-2,-2,-5,-1,-1,-2,-2,-3
      2, 2, 1, 5, 5, 2, 0, 0, 0,-2,-5,-1,-1,-2,-2,-2,-3,-3,-3
      1, 1, 5, 2, 0, 0, 0,-5,-2,-5,-1,-2,-2,-2,-3,-3,-3,-4,-4
     -1,-1,-1,-5,-5,-5,-1,-1,-1,-2,-3,-3,-3,-3,-4,-4,-4,-4
     -2,-2,-1,-1,-5,-1,-1,-2,-2,-2,-3,-3,-4,-4,-4,-4,-4,-4
     -3,-2,-2,-1,-1,-2,-2,-3,-3,-4,-4,-4,-5,-5,-5,-5,-5,-5
     -3,-3,-3,-2,-2,-3,-3,-4,-4,-4,-5,-5,-5,-5,-5,-5,-5,-5
     -4,-3,-3,-3,-3,-4,-4,-5,-5,-5,-5,-5,-5,-5,-5,-5,-5,-5
     -4,-3,-3,-4,-4,-4,-5,-5,-5,-5,-5,-5,-5,-5,-5,-5,-5,-8
     -4,-4,-4,-5,-5,-5,-5,-5,-5,-5,-5,-5,-5,-5,-5,-5,-8,-10
```

Table 1 is non-linear and allows the appropriate control action given the error and change in error in the previous scan. The Table is read and the control change signal value is selected. Different accelerations and braking occur when approaching the target from different directions. Table 1 is symmetric with a starting point based on a proven control. In another embodiment, the table is non-symmetric and non-linear response gains in positive or negative directions can be increased or decreased as needed. A scaling factor may be applied to the control change signal to allow the entire Table magnitude to be normalized to a specific process system.

Various changes may be made to the embodiments shown herein without departing from the scope of the present invention which is limited only by the following claims.

The embodiments of the present invention in which an exclusive property or privilege is claimed are defined as follows:

1. A method of reducing start up time for bringing a caliper profile across a width of a paper sheet to within predetermined limits on a paper machine, comprising the steps of:

scanning at predetermined intervals across the width of the paper sheet to monitor thickness error of the sheet from the predetermined limits, and change in the thickness error between the intervals, in each of a plurality of zones across the sheet;

determining a control change signal in each of the zones based on the error and the change in the error using an exponential function of magnitude of the error to maximize the change in the error and reduce integral action when the error is large, said control change signal being determined according to the formula:

$$c(t)=K_p[(e(t)-e(t-1))+K_I e(t)]$$

where $K_p$ is a process gain factor, e(t) is the error for one scan, e(t−1) is the error for the previous scan, $K_I$ is a function of the error and equals:

$$\exp\frac{(-e(t))}{\lambda} \times K_{IO}$$

where $K_{IO}$ is the nominal $K_I$ gain when the error is small and $\lambda$ is a gain scaling factor;

utilizing the control change signal to reduce the error in each of the zones; and increasing the integral action in each of the zones as the error decreases until the predetermined limits are met.

2. The method of reducing start up time according to claim 1 wherein the gain scaling factor ($\lambda$) is in the range of about 0.5 to 10.

3. The method of reducing start up time according to claim 1 wherein the control change signal is selected from a predetermined Table of errors and changes in the errors determined according to the formula.

4. A control system which reduces start up time to bring caliper a profile across a width of a paper sheet to within predetermined limits on a paper machine comprising:

scanning means to scan across the width of the paper sheet at predetermined intervals and produce error signals representing thickness error of the sheet from the predetermined limits in a plurality of zones across the sheet;

means to determine change in the error in each of the zones from scan to scan;

optimizer means to maximize the change in the error in each of the zones, when the error is large, by modifying the change in error as a function of the error to provide a control change signal which is limited, based on magnitude of the error, by reducing integral action when the error is large, the integral action increasing as the error decreases, wherein the control change signal from the error and the change in error in each of the zones is determined according to the formula:

$$c(t)=K_p[(e(t-e(t-1))+K_I e(t)]$$

where $K_p$ is a process gain factor, $e(t)$ is the error for one scan, $e(t-1)$ is the error for the previous scan, $K_I$ is a function of the error and equals:

$$\exp\frac{(-e(t))}{\lambda} \times K_{IO}$$

where $K_{IO}$ is the nominal $K_I$ gain when the error is small and $\lambda$ is a gain scaling factor; and control means utilizing the control change signal to reduce the error in each of the zones until the predetermined limits are met, wherein the control means includes heating means to heat each of the zones across a roll surface in accordance with the control change signal.

5. The control system which reduces start up time according to claim 4 including a selector to select the control change signal from a predetermined table of errors and changes in the errors determined according to the formula.

* * * * *